United States Patent
Berends, Jr.

(10) Patent No.: US 7,568,401 B1
(45) Date of Patent: Aug. 4, 2009

(54) SAMPLE TUBE HOLDER

(75) Inventor: John C. Berends, Jr., Bel Air, MD (US)

(73) Assignee: Science Applications International Corporation, San Diego, CA (US)

( * ) Notice: Subject to any disclaimer, the term of this patent is extended or adjusted under 35 U.S.C. 154(b) by 474 days.

(21) Appl. No.: 11/455,334

(22) Filed: Jun. 19, 2006

Related U.S. Application Data

(60) Provisional application No. 60/692,166, filed on Jun. 20, 2005.

(51) Int. Cl.
*G01N 1/00* (2006.01)
(52) U.S. Cl. .................................................. 73/863.21
(58) Field of Classification Search ........................ None
See application file for complete search history.

(56) References Cited

U.S. PATENT DOCUMENTS

| | | | | |
|---|---|---|---|---|
| 4,000,918 A | * | 1/1977 | Reker | 285/93 |
| 4,159,423 A | | 6/1979 | Kambara | 250/423 R |
| 4,209,696 A | | 6/1980 | Fite | 250/281 |
| 4,256,335 A | * | 3/1981 | Nielsen, Jr. | 285/250 |
| 4,271,357 A | | 6/1981 | Bradshaw et al. | 250/287 |
| 4,300,004 A | | 11/1981 | Wissner et al. | 570/211 |
| 4,318,028 A | | 3/1982 | Perel et al. | 315/111.81 |
| 4,468,468 A | | 8/1984 | Benninghoven et al. | 436/173 |
| 4,531,056 A | | 7/1985 | Labowsky et al. | 250/288 |
| 4,542,293 A | | 9/1985 | Fenn et al. | 250/288 |
| 4,546,253 A | | 10/1985 | Tsuchiya et al. | 250/288 |
| 4,789,783 A | | 12/1988 | Cook | 250/379 |
| 4,855,595 A | | 8/1989 | Blanchard | 250/287 |
| 4,948,962 A | | 8/1990 | Mitsui et al. | 250/288 |
| 4,974,648 A | | 12/1990 | Propst | 144/24.13 |
| 4,976,920 A | | 12/1990 | Jacob | 422/23 |
| 4,977,320 A | | 12/1990 | Chowdhury et al. | 250/288 |
| 4,999,492 A | | 3/1991 | Nakagawa | 250/281 |
| 5,141,532 A | * | 8/1992 | Sacks et al. | 95/87 |
| 5,142,143 A | * | 8/1992 | Fite et al. | 250/288 |
| 5,164,704 A | | 11/1992 | Steen et al. | 340/539.17 |
| 5,168,068 A | * | 12/1992 | Yanagisawa et al. | 436/134 |
| 5,171,525 A | | 12/1992 | Jacob | 422/23 |

(Continued)

FOREIGN PATENT DOCUMENTS

GB 2127212 4/1984

(Continued)

OTHER PUBLICATIONS

Application as Filed for U.S. Appl. No. 11/987,632, filed Dec. 3, 2007, 46 pp.

(Continued)

*Primary Examiner*—Robert R Raevis
(74) *Attorney, Agent, or Firm*—King & Spalding LLP

(57) ABSTRACT

A sorbent-filled sample tube is mounted to an aspirating source using a sample tube holder that includes a compression fitting having a fitting body, a cap, and a ferrule. The fitting cap is extended as a torque tube that surrounds the sample tube and has a length approximately equal to that of the sample tube to thereby protect the sample tube from damage. The free end of the torque tube is formed as a thumb wheel for ease in inserting and removing the sample tube without the use of a wrench or other tool.

10 Claims, 1 Drawing Sheet

U.S. PATENT DOCUMENTS

| | | | |
|---|---|---|---|
| 5,192,865 A | 3/1993 | Zhu | 250/288 |
| 5,280,175 A | 1/1994 | Karl | 250/287 |
| 5,304,797 A | 4/1994 | Irie et al. | 250/287 |
| 5,305,015 A | 4/1994 | Schantz et al. | 347/47 |
| 5,306,910 A | 4/1994 | Jarrell et al. | 250/286 |
| 5,338,931 A | 8/1994 | Spangler et al. | 250/287 |
| 5,412,208 A | 5/1995 | Covey et al. | 250/288 |
| 5,412,209 A | 5/1995 | Otaka et al. | 250/310 |
| 5,436,446 A | 7/1995 | Jarrell et al. | 250/288 |
| 5,485,016 A | 1/1996 | Irie et al. | 250/288 |
| 5,541,519 A | 7/1996 | Stearns et al. | 324/464 |
| 5,559,326 A | 9/1996 | Goodley et al. | 250/288 |
| 5,581,081 A | 12/1996 | Kato et al. | 250/288 |
| 5,587,581 A | 12/1996 | Stroosnyder | 250/287 |
| 5,625,184 A | 4/1997 | Vestal et al. | 250/287 |
| 5,684,300 A | 11/1997 | Taylor et al. | 250/286 |
| 5,736,740 A | 4/1998 | Franzen | 250/288 |
| 5,747,799 A | 5/1998 | Franzen | 250/288 |
| 5,750,988 A | 5/1998 | Apffel et al. | 250/288 |
| 5,753,910 A | 5/1998 | Gourley et al. | 250/288 |
| 5,756,994 A | 5/1998 | Bajic | 250/288 |
| 5,798,146 A | 8/1998 | Murokh et al. | 427/458 |
| 5,828,062 A | 10/1998 | Jarrell et al. | 250/288 |
| 5,838,002 A | 11/1998 | Sheehan | 250/288 |
| 5,873,523 A | 2/1999 | Gomez et al. | 239/3 |
| 5,892,364 A | 4/1999 | Monagle | 324/464 |
| 5,945,678 A | 8/1999 | Yanagisawa | 250/423 F |
| 5,965,884 A | 10/1999 | Laiko et al. | 250/288 |
| 5,986,259 A | 11/1999 | Hirabayachi et al. | 250/288 |
| 6,040,575 A | 3/2000 | Whitehouse et al. | 250/288 |
| 6,060,705 A | 5/2000 | Whitehouse et al. | 250/288 |
| 6,107,628 A | 8/2000 | Smith et al. | 250/292 |
| 6,124,675 A | 9/2000 | Bertrand et al. | 315/111.91 |
| 6,147,345 A | 11/2000 | Willoughby | 250/288 |
| 6,204,500 B1 | 3/2001 | Whitehouse et al. | 250/287 |
| 6,207,954 B1 | 3/2001 | Andrien, Jr. et al. | 250/288 |
| 6,223,584 B1* | 5/2001 | Mustacich et al. | 73/23.41 |
| 6,225,623 B1 | 5/2001 | Turner et al. | 250/286 |
| 6,239,428 B1 | 5/2001 | Kunz | 250/287 |
| 6,278,111 B1 | 8/2001 | Sheehan et al. | 250/288 |
| 6,359,275 B1 | 3/2002 | Bertsch et al. | 250/281 |
| 6,455,846 B1 | 9/2002 | Prior et al. | 250/288 |
| 6,462,338 B1 | 10/2002 | Inatsugu et al. | 250/292 |
| 6,465,776 B1 | 10/2002 | Moini et al. | 250/285 |
| 6,486,469 B1 | 11/2002 | Fischer et al. | 250/288 |
| 6,495,823 B1 | 12/2002 | Miller et al. | 250/286 |
| 6,512,224 B1 | 1/2003 | Miller et al. | 250/286 |
| 6,534,765 B1 | 3/2003 | Robb et al. | 250/288 |
| 6,537,817 B1 | 3/2003 | Papen | 436/49 |
| 6,583,407 B1 | 6/2003 | Fischer et al. | 250/288 |
| 6,583,408 B2 | 6/2003 | Smith et al. | 250/288 |
| 6,600,155 B1 | 7/2003 | Andrien, Jr. et al. | 250/287 |
| 6,610,986 B2 | 8/2003 | Hartley | 250/423 R |
| 6,649,907 B2 | 11/2003 | Ebeling et al. | 250/288 |
| 6,683,301 B2 | 1/2004 | Whitehouse et al. | 250/288 |
| 6,690,004 B2 | 2/2004 | Miller et al. | 250/286 |
| 6,727,496 B2 | 4/2004 | Miller et al. | 250/287 |
| 6,744,041 B2 | 6/2004 | Sheehan et al. | 250/283 |
| 6,750,449 B2 | 6/2004 | Marcus | 250/288 |
| 6,784,424 B1 | 8/2004 | Willoughby et al. | 250/292 |
| 6,815,668 B2 | 11/2004 | Miller et al. | 250/286 |
| 6,818,889 B1 | 11/2004 | Sheehan et al. | 250/288 |
| 6,822,225 B2 | 11/2004 | Xu et al. | 250/287 |
| 6,852,969 B2 | 2/2005 | Marcus et al. | 250/288 |
| 6,852,970 B2 | 2/2005 | Yamada et al. | 250/288 |
| 6,867,415 B2 | 3/2005 | Hughey et al. | 250/288 |
| 6,878,930 B1 | 4/2005 | Willoughby et al. | 250/281 |
| 6,888,132 B1 | 5/2005 | Sheehan et al. | 250/288 |
| 6,914,243 B2 | 7/2005 | Sheehan et al. | 250/288 |
| 6,943,347 B1 | 9/2005 | Willoughby et al. | 250/288 |
| 6,949,740 B1 | 9/2005 | Sheehan et al. | 250/288 |
| 6,949,741 B2 | 9/2005 | Cody et al. | 250/288 |
| 6,972,407 B2 | 12/2005 | Miller et al. | 250/287 |
| 6,998,605 B1 | 2/2006 | Frazer et al. | 250/281 |
| 7,005,634 B2 | 2/2006 | Shiokawa et al. | 250/288 |
| 7,041,966 B2 | 5/2006 | Frazer et al. | 250/281 |
| 7,053,367 B2 | 5/2006 | Tobita et al. | 250/288 |
| 7,060,976 B2 | 6/2006 | Sheehan et al. | 250/288 |
| 7,064,320 B2 | 6/2006 | Yamada et al. | 250/288 |
| 7,078,068 B2 | 7/2006 | Book | 426/140 |
| 7,083,112 B2 | 8/2006 | Ivri | 239/4 |
| 7,087,898 B2 | 8/2006 | Willoughby et al. | 250/288 |
| 7,091,493 B2 | 8/2006 | Hiraoka | 250/425 |
| 7,095,019 B1 | 8/2006 | Sheehan et al. | 250/288 |
| 7,112,785 B2 | 9/2006 | Laramee et al. | 250/288 |
| 7,112,786 B2 | 9/2006 | Russ, IV et al. | 250/288 |
| 7,138,626 B2 | 11/2006 | Karpetsky | 250/288 |
| 7,253,406 B1 | 8/2007 | Sheehan et al. | 250/288 |
| 7,259,368 B2 | 8/2007 | Frazer et al. | 250/281 |
| 7,274,015 B2 | 9/2007 | Miller et al. | 356/508 |
| 7,429,731 B1 | 9/2008 | Karpetsky | 250/288 |
| 2002/0011560 A1 | 1/2002 | Sheehan et al. | 250/283 |
| 2002/0175278 A1 | 11/2002 | Whitehouse | 250/281 |
| 2002/0185593 A1 | 12/2002 | Doring | 250/287 |
| 2002/0185595 A1 | 12/2002 | Smith et al. | 250/288 |
| 2003/0034452 A1 | 2/2003 | Fischer et al. | 250/288 |
| 2003/0038236 A1 | 2/2003 | Russ, IV et al. | 250/288 |
| 2003/0197121 A1 | 10/2003 | Turecek et al. | 250/281 |
| 2004/0161856 A1* | 8/2004 | Handly | 436/177 |
| 2004/0245458 A1 | 12/2004 | Sheehan et al. | 250/288 |
| 2005/0056775 A1 | 3/2005 | Cody et al. | 250/281 |
| 2005/0196871 A1 | 9/2005 | Cody et al. | 436/173 |
| 2006/0249671 A1 | 11/2006 | Karpetsky | 250/288 |
| 2007/0084999 A1 | 4/2007 | Miller et al. | 250/288 |
| 2007/0114389 A1 | 5/2007 | Karpetsky et al. | 250/288 |
| 2008/0296493 A1 | 12/2008 | Willoughby et al. | 250/288 |

FOREIGN PATENT DOCUMENTS

| | | |
|---|---|---|
| GB | 2288061 | 10/1995 |
| JP | 04215329 | 8/1992 |
| JP | 05203637 | 8/1993 |
| JP | 10088798 | 4/1998 |
| WO | WO 93/14515 | 7/1993 |
| WO | WO 98/07505 | 2/1998 |
| WO | WO 99/63576 | 12/1999 |
| WO | WO 00/08455 | 2/2000 |
| WO | WO 00/08456 | 2/2000 |
| WO | WO 00/08457 | 2/2000 |
| WO | WO 01/33605 A2 | 5/2001 |
| WO | WO 01/33605 A3 | 5/2001 |
| WO | WO 03/010794 | 2/2003 |
| WO | WO 2004/098743 | 11/2004 |
| WO | WO 2004/110583 | 12/2004 |
| WO | WO 2006/011171 | 2/2006 |
| WO | WO 2006/122121 | 11/2006 |
| WO | WO 2008/054393 | 5/2008 |

OTHER PUBLICATIONS

Application as Filed for U.S. Appl. No. 11/544,252, filed Oct. 7, 2006, 49 pp.

Application as Filed for U.S. Appl. No. 11/594,401, filed Nov. 8, 2006, 23 pp.

Application as Filed for U.S. Appl. No. 12/153,358, filed May 16, 2008, 46 pp.

Application as Filed for U.S. Appl. No. 12/200,941, filed Aug. 29, 2008, 21 pp.

Application as Filed for U.S. Appl. No. 12/344,872, filed Dec. 29, 2008, 39 pp.

Hanson, Eric, "How an Ink Jet Printer Works" [online], [retrieved on May 15, 2008], 5 pp., Retrieved from the Internet: http://www.imaging.org/resources/web_tutorials/inkjet_files/inkjet.cfm.

Le, Hue P., "Progress and Trends in Ink-Jet Printing Technology" [online], *Journal of Imaging Science and Technology*, vol. 42, No. 1, Jan./Feb. 1998 [retrieved on May 15, 2008], 28 pp, Retrieved from the Internet: http://www.imaging.org/resources/web_tutorials/inkjet.cfm.

Chemi-Ionization—Mass Spectrometry Terms, "Chemi-Ionization" [online], Dec. 26, 2005 [retrieved on Apr. 28, 2006], 1 p., Retrieved from the Internet: http://www.msterms.com/wiki/index.php?title=Chemi-Ionization.

Scott, R.P.W., "Gas Chromatography Detectors" [online], Part of the Chrom. Ed. Series, Subsection: Thermal Argon Detector, Copyright 2002-2005 [retrieved on Apr. 28, 2006], 7 pp., Retrieved from the Internet: http://www.chromatography-online.org/GC-Detectors/Ionization-Detectors/Thermal-Argon/rs61.html.

Scott, R.P.W., "Gas Chromatography Detectors" [online], Part of the Chrom. Ed. Series, Subsection: Macro Argon Detector, Copyright 2002-2005 [retrieved on Apr. 28, 2006], 10 pp., Retrieved from the Internet: http://www.chromatography-online.org/GC-Detectors/Ionization-Detectors/Macro-Argon/rs54.html.

Scott, R.P.W., "Gas Chromatography Detectors" [online], Part of the Chrom. Ed. Series, Subsection: Micro Argon Detector, Copyright 2002-2005 [retrieved on May 11, 2006], 6 pp., Retrieved from the Internet: http://www.chromatography-online.org/GC-Detectors/Ionization-Detectors/Micro-Argon/rs59.html.

Scott, R.P.W., "Gas Chromatography Detectors"[online], Part of the Chrom. Ed. Series, Subsection: The Helium Detector, Copyright 2002-2005 [retrieved on Apr, 28, 2006], 8 pp., Retrieved from the Internet: http://www.chromatography-online.org/GC-Detectors/Ionization-Detectors/Helium/rs64.html.

Laroussi, M., and Lu, X., "Room-Temperature Atmospheric Pressure Plasma Plume for Biomedical Applications," *Applied Physics Letters* 87, 113902, Sep. 8, 2005.

Akishev, Yu, et al., "Negative Corona, Glow and Spark Discharges in Ambient Air and Transitions Between Them," *Plasma Sources Sci. Technol.*, vol. 14, pp. S18-S25 (2005).

Willoughby, Ross C., et al., "Transmission of Ions Through Conductance Pathways from Atmospheric Pressure," *Proceedings of the 52$^{nd}$ ASMS Conference on Mass Spectrometry and Allied Topics* , Nashville, Tennessee, 2 pp., May 23-27, 2004.

Sheehan, Edward W., et al., "Atmospheric Pressure Focusing," *Proceedings of the 52$^{nd}$ ASMS Conference on Mass Spectrometry and Allied Topics*, Nashville, Tennessee, 2 pp., May 23-27, 2004.

Benocci, R., et al., "I-V Characteristics and Photocurrents of a He Corona Discharge Under Flow Conditions," *J. Phys. D: Appl. Phys.*, vol. 37, pp. 709-714 (2004).

Bokman, C. Fredrik, "Analytical Aspects of Atmospheric Pressure Ionization in Mass Spectrometry," Acta Universitatis Upsaliensis, *Comprehensive Summaries of Uppsala Dissertations from the Faculty of Science and Technology*, vol. 748, 46 pp., 2002.

Willoughby, R., Sheehan, E., Mitrovich, A., "A Global View of LC/MS," Global View Publishing, pp. 64-65, 470-471, Copyright 2002.

Stach, J., et al., "Ion Mobility Spectrometry—Basic Elements and Applications," *International Journal for Ion Mobility Spectrometry*, IJIMS 5(2002)1, pp. 1-21, 2002.

Hanley, Luke, et al., "Surface Mass Spectrometry of Molecular Species," *Journal of Mass Spectrometry*, vol. 34, pp. 705-723 (1999).

Steinfeld, Jeffrey I., et al., "Explosives Detection: A Challenge for Physical Chemistry," *Annual Review of Physical Chemistry*, vol. 49, pp. 203-232, Oct. 1998.

Lin, B., Sunner, J., "Ion Transport by Viscous Gas Flow Through Capillaries," *J. Am. Soc. Mass Spectrom.* 5, pp. 873-885 (1994).

Potjewyd, J., "Focusing of Ions in Atmospheric Pressure Gases Using Electrostatic Fields," Ph.D. Thesis, University of Toronto (1983).

Mahoney, J. F., et al., "A Theoretical and Experimental Basis for Producing Very High Mass Biomolecular Ions by Electrohydrodynamic Emission," *22$^{nd}$ IEEE Industry Applications Society Annual Meeting*, Atlanta, Georgia, Oct. 18-23, 1987.

Olivares, J. A., et al., "On-Line Mass Spectrometric Detection for Capillary Zone Electrophoresis," *Anal. Chem.* 59, pp. 1230-1232 (1987).

Lee, T. D., et al., "An EHD Source for the Mass Spectral Analysis of Peptides," *Proceedings of the 36$^{th}$ ASMS Conference on Mass Spectrometry and Allied Topics*, San Francisco, California, Jun. 5-10, 1988.

Smith, R. D., et al., "Capillary Zone Electrophoresis-Mass Spectrometry Using an Electrospray Ionization Interface," *Anal. Chem.* 60, pp. 436-441 (1988).

Lee, T. D., et al. "Electrohydrodynamic Emission Mass Spectra of Peptides," *Proceedings of the 37$^{th}$ ASMS Conference on Mass Spectrometry and Allied Topics*, Miami Beach, Florida, May 21-26, 1989.

Mahoney, J. F., et al., "Electrohydrodynamic Ion Source Design for Mass Spectrometry: Ionization, Ion Optics and Desolvation," *Proceedings of the 38$^{th}$ ASMS Conference on Mass Spectrometry and Allied Topics*, Tucson, Arizona, Jun. 3-8, 1990.

Feng, X., et al., "Single Isolated Droplets with Net Charge as a Source of Ions," *J. Am. Soc. Mass Spectrom*, 11, pp. 393-399 (2000).

Schneider, B. B., et al., "An Atmospheric Pressure Ion Lens to Improve Electrospray Ionization at Low Solution Flow-Rates," *Rapid Commun. Mass Spectrom* 15, pp. 2168-2175 (2001).

Alousi, A., et al., "Improved Transport of Atmospheric Pressure Ions Into a Mass Spectrometer," *The Proceedings of the 50$^{th}$ ASMS Conference on Mass Spectrometry and Allied Topics*, Orlando Florida, Jun. 2-6, 2002.

Klesper, H., et al., "Intensity Increase in ESI MS by Means of Focusing the Spray Cloud onto the MS Orifice," *The Proceeding of the 50$^{th}$ ASMS Conference on Mass Spectrometry and Allied Topics*, Orlando, Florida, Jun. 2-6, 2002.

Schneider, B. B., et al., "An Atmospheric Pressure Ion Lens that Improves Nebulizer Assisted Electrospray Ion Sources," *J. Am. Soc. Mass Spectrom.* 13, pp. 906-913 (2002).

Hartley, F. T., et al., "NBC Detection in Air and Water," *Micro/Nano* 8, pp. 1, 2, and 8 (Dec. 2003).

Cody, R. B., et al., "Versatile New Ion Source for the Analysis of Materials in Open Air Under Ambient Conditions," *Anal. Chem.* 77, pp. 2297-2302 (2005).

McEwen, C. N., et al., "Analysis of Solids, Liquids, and Biological Tissues Using Solids Probe Introduction at Atmospheric Pressure . . . ," *Anal. Chem.* 77, pp. 7826-7831 (2005).

Niessen, W.M.A. and van der Greef, J., "Liquid Chromatography—Mass Spectrometry Principles and Applications," Marcel Dekker, Inc., New York, New York, pp. 339-341, Copyright 1992.

Hart, K. J., et al., "Reaction of Analyte Ions With Neutral Chemical Ionization Gas," *Journal of the American Society for Mass Spectrometry*, vol. 3, No. 5, pp. 549-557, 1992 (ISSN 1044-0305).

Bruins, A.P., "Mass Spectrometry With Ion Sources Operating at Atmospheric Pressure," *Mass Spectrometry Reviews*, vol. 10, pp. 53-77, 1991.

Duckworth, D. C., et al., "Radio Frequency Powered Glow Discharge Atomization/Ionization Source for Solids Mass Spectrometry," *Analytical Chemistry*, vol. 61, No. 17, pp. 1879-1886, Sep. 1, 1989.

Beres, S.A., et al., "A New Type of Argon Ionisation Detector," *Analyst*, vol. 112, pp. 91-95, Jan. 1987.

Lovelock, J.E. and Lipsky, S.R., "Electron Affinity Spectroscopy—A New Method for the Identification of Functional Groups in Chemical Compounds Separated by Gas Chromatography," *J. Amer. Chem. Soc.*, vol. 82, pp. 431-433, Jan. 20, 1960.

Lovelock, J.E., "A Sensitive Detector for Gas Chromatrography," *Journal of Chromatography*, vol. 1, pp. 35-46, 1958.

Lovelock, J.E., "Measurement of Low Vapour Concentrations by Collision with Excited Rare Gas Atoms," *Nature*, vol. 181, pp. 1460-1462, 1958.

Cody, et al., "DART™: Direct Analysis in Real Time for Drugs, Explosives, Chemical Agents, and More . . . ," Sanibel Conference (American Society for Mass Spectrometry Sanibel Conference on Mass Spectrometry in Forensic Science and Counter-Terrorism), Clearwater, Florida, 39 pp., Jan. 28-Feb. 1, 2004.

* cited by examiner

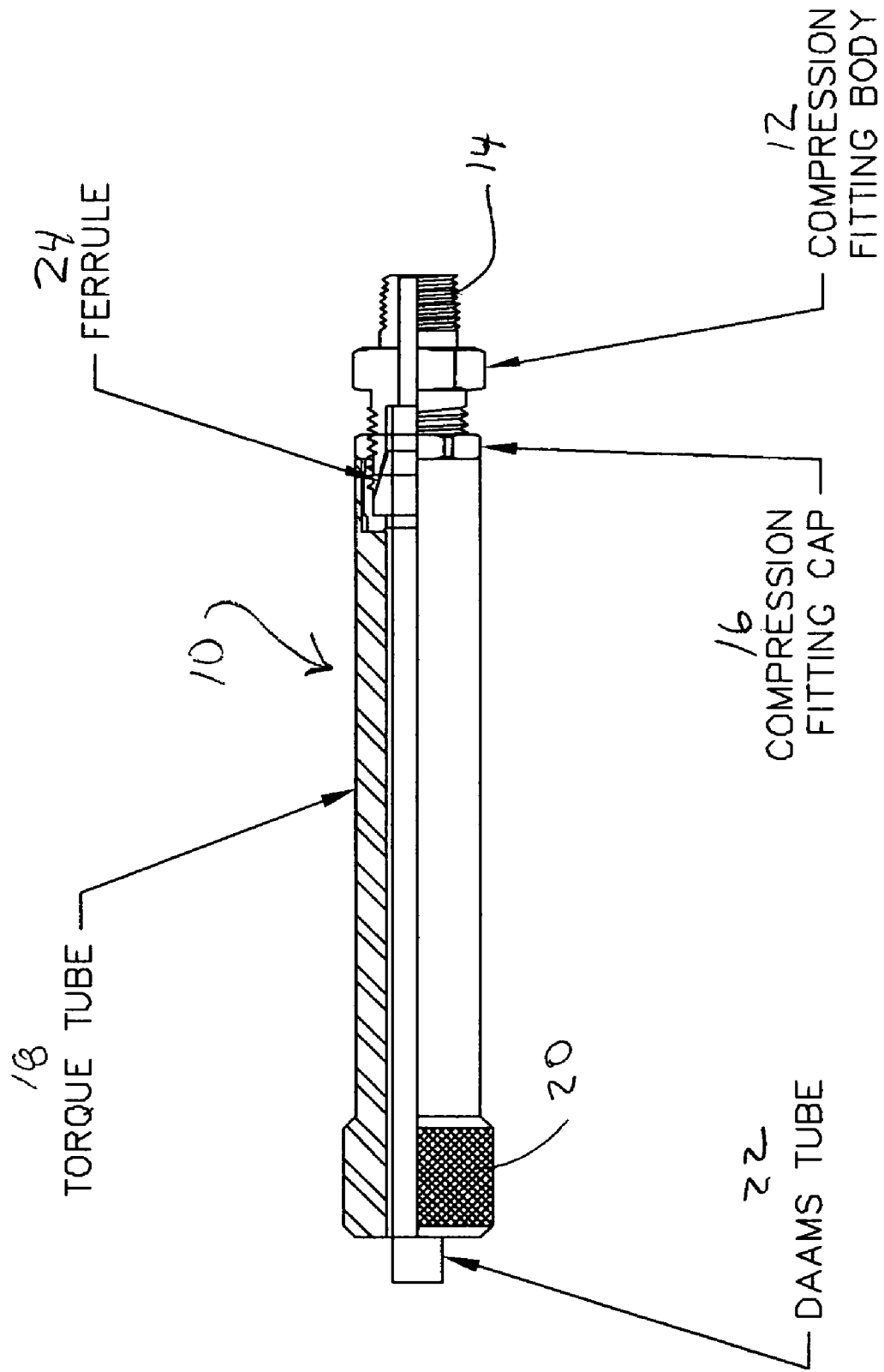

SAMPLE TUBE HOLDER

REFERENCE TO RELATED APPLICATION

This application claims the benefit of U.S. Provisional Patent Application No. 60/692,166 that was filed Jun. 20, 2005.

BACKGROUND OF THE INVENTION

1. Technical Field

This invention relates to an improvement in devices for monitoring air and other gases.

More particularly, this invention relates to an improvement to the mounting means for a sampling tube used in an air or industrial gas monitoring system.

2. Description of Related Art

A common method for monitoring air and other gas streams to detect the presence of chemical agents, toxic industrial chemicals, and other compounds that might be of interest employs sorbent-packed tubes for sample collection. Those sample tubes, commonly referred to as DMMS tubes (an acronym for depot area air monitoring system) comprise a glass or stainless steel tube that is filled with a solid adsorbent such as activated carbon or a molecular sieve. The adsorbent filling is selected according to the chemicals that are being monitored.

A sample is collected by aspirating air or other sample gas through the tube for a predetermined period of time at a controlled gas flow rate. Vapors of the compounds of interest are adsorbed on the solid sorbent, and the sample tube is then removed from its sampling site for its analysis in a laboratory. The laboratory procedure commonly employed thermally desorbs the sample and passes it into an analytical system which may be, for example, gas chromatography, or gas chromatography in combination with mass spectrometry.

In field use, one end of a sample tube is connected to a vacuum manifold that maintains a known negative pressure relative to the atmosphere being sampled. If the seal between the sample tube and the manifold is not secure and leakage occurs, then the sample results are compromised and cannot be trusted. Forming a secure seal on the end of a sample tube is difficult because an end seal requires that the tube end meet strict requirements for flatness and squareness. A chip or other imperfection on the tube end creates a potential leakage site causing an end seal to fail. It is also possible to use an O-ring to form a seal on the outside diameter of the tube, but that type of seal often makes it difficult to insert the tube end into and to remove it from a mating fitting on the vacuum manifold. That is particularly true if the tube is enclosed in some manner in order to protect it from physical damage. Another complication arises from the fact that variation in the length of sample tubes is common.

The device disclosed and claimed in this application overcomes all of those problems, and does so in a simple, dependable, and cost effective manner.

SUMMARY OF THE INVENTION

This sample tube mounting means of this invention comprises a compression fitting having an elastomeric ferrule into which a sorbent-filled sample tube is inserted. The cap member of the compression fitting is extended as a torque tube that fits over and protects the sample tube. The free end of the torque tube extension is preferably formed as a thumb wheel for ease in removal and replacement of the sample tube without the use of tools

BRIEF DESCRIPTION OF THE DRAWING

The sole FIGURE is a partial sectional view of the sample tube holder according to this invention.

DETAILED DESCRIPTION OF THE INVENTION

This invention will be described with reference to the drawing FIGURE where the sample tube holder is shown in a partial cross-sectional view at 10. The tube holder includes a compression fitting body 12 having an end 14 that is adapted for connection to a source of vacuum such as a vacuum manifold (not shown.) End 14 may be threaded as shown in the drawing or may comprise any other gas tight connection means such as a snap coupling or the like. The other end of the compression fitting body 12 is adapted to accept and seat an end of a sample tube and to provide communication between the vacuum source and the seated tube end. Fitting body 12 is threaded for connection to a compression fitting cap 16 that is extended as a torque tube 18. The free end of torque tube 18 opposite fitting cap 16 preferably terminates as a thumb wheel 20. Wheel 20 may be provided with a knurled or otherwise patterned surface for ease in gripping and turning without use of a wrench or other tool.

The inside diameter of torque tube 18 is sized somewhat larger than the exterior diameter of a sorbent-filled sample tube, such as a DAAMS tube 22, to allow for easy insertion and removal of the tube. An elastomeric ferrule 24, sized to make a sliding fit with the exterior of tube 22, is seated within compression fitting cap 16 adjacent the tube end that extends into the body 12 of the compression fitting. It is preferred that the ferrule be fabricated from a chemically inert material such as Vespel® or Teflon®. As the torque tube is tightened, the ferrule is compressed about the exterior of the sample tube to thereby provide a gas-tight seal between the tube end and the vacuum source. It is preferred that the length of torque tube 18 be approximately the same as that of the sample tube to thereby provide maximum physical protection for the sample tube while not interfering with its insertion into or removal from the fitting site.

In use, a fresh sample tube is connected to a vacuum source using the sample tube holder of this invention. A stream of gas from the atmosphere being sampled is drawn through the tube by the pressure differential between the vacuum source and the atmosphere being sampled for a predetermined time period to adsorb upon the tube packing those atmospheric components that are being monitored. The loaded sorbent tube is then removed from the sample tube holder, is replaced with a fresh tube, and the loaded tube is transported to a laboratory or other analysis site. The cycle then is repeated.

As may now be appreciated, the sample tube holder of this invention provides a convenient and practical means for connecting a sorbent-filled sample tube to a vacuum source and to facilitate its exchange with a fresh tube while also protecting it from physical damage during the sampling procedure.

It will be understood that the specific embodiments described herein are exemplary and that persons skilled in the art may make variations and modifications that have not been specifically described without departing from the spirit and scope of the invention as is defined by the following claims.

The invention claimed is:

1. A sample tube holder comprising:
   a compression fitting body, one end of said body arranged for connection to a vacuum source and the other end of said body arranged to accept and seat a first end of a sorbent-filled sample tube, said fitting body providing communication between the vacuum source and the sample tube;

an elastomeric ferrule adapted for fitting about the exterior of said sample tube adjacent the seated first end thereof, the other end of the sample tube open to the atmosphere being sampled;

a compression fitting cap engaging the fitting body to compress said ferrule and provide a gas tight seal between the vacuum source and the sample tube first end; and a torque tube formed as an extension of said fitting cap, the inside diameter of said torque tube sized to fit over the sample tube, said torque tube having a length substantially the same as that of the sample tube.

2. The sample tube holder of claim 1 wherein the free end of said torque tube opposite said fitting cap end is formed as a thumb wheel.

3. The sample tube holder of claim 2 wherein said thumb wheel is knurled or patterned for ease in hand operation.

4. The sample tube holder of claim 1 wherein said compression fitting body end is threaded for connection to a vacuum source.

5. The sample tube holder of claim 1 wherein said elastomeric ferrule is chemically inert.

6. A holder for a DAAMS tube comprising:

a compression fitting body, one end of said fitting body threaded for connection to a vacuum source, and the other end of said fitting body sized to accept and seat one end of a DAAMS tube, the fitting body providing communication between the vacuum source and the DAAMS tube end;

a chemically inert, elastomeric ferrule adapted for fitting about the exterior of said DAAMS tube adjacent its seated end;

a compression fitting cap arranged to engage the fitting body to compress said ferrule and to provide a gas tight seal between the vacuum source and the seated end of the DAAMS tube; and a torque tube formed as an extension of said fitting cap, the inside diameter of said torque tube sized to fit over the sample tube, said torque tube having a length substantially the same as that of the DAAMS tube.

7. The holder of claim 6 wherein the ferrule is fabricated of Teflon®.

8. The holder of claim 6 wherein the ferrule is fabricated of Vespel®.

9. The holder of claim 6 wherein the free end of said torque tube opposite said fitting cap end is formed as a thumb wheel.

10. The holder of claim 9 wherein said thumb wheel is knurled or patterned for ease in hand operation.

* * * * *